(12) United States Patent
Heeres et al.

(10) Patent No.: US 8,828,982 B2
(45) Date of Patent: Sep. 9, 2014

(54) PYRIMIDINE DERIVATIVES FOR THE PREVENTION OF HIV INFECTION

(75) Inventors: Jan Heeres, Vosselaar (BE); Paulus Joannes Lewi, Turnhout (BE); Paul Adriaan Jan Janssen, Vosselaar (BE); Frank Xavier Jozef Herwig Arts, legal representative, Brasschaat (BE); Marc René de Jonge, Tilburg (NL); Lucien Maria Henricus Koymans, Retie (BE); Frederik Frans Desiré Daeyaert, Beerse (BE); Hendrik Maarten Vinkers, Antwerp (BE); Jérôme Emile Georges Guillemont, Ande (FR); Elisabeth Therese Jeanne Pasquier, Le Neubourg (FR)

(73) Assignee: Janssen Pharmaceutica N.V., Beerse (BE)

( * ) Notice: Subject to any disclaimer, the term of this patent is extended or adjusted under 35 U.S.C. 154(b) by 994 days.

(21) Appl. No.: 12/567,051

(22) Filed: Sep. 25, 2009

(65) Prior Publication Data

US 2010/0034810 A1    Feb. 11, 2010

Related U.S. Application Data

(63) Continuation of application No. 10/544,735, filed as application No. PCT/EP2004/001011 on Feb. 4, 2004, now abandoned.

(30) Foreign Application Priority Data

Feb. 7, 2003 (WO) ........................ PCT/EP03/01291

(51) Int. Cl.
  *A01N 43/00* (2006.01)
  *A61K 31/33* (2006.01)
  *A61K 39/395* (2006.01)
(52) U.S. Cl.
  USPC ........................................ 514/183; 424/130.1
(58) Field of Classification Search
  USPC ........................................ 514/183; 424/130.1
  See application file for complete search history.

(56) References Cited

U.S. PATENT DOCUMENTS

| | | | |
|---|---|---|---|
| 3,459,731 A | 8/1969 | Gramera et al. |
| 3,459,732 A | 8/1969 | Hull et al. |
| 4,952,411 A | 8/1990 | Fox, Jr. et al. |
| 5,691,364 A | 11/1997 | Buckman et al. |
| 2006/0166943 A1 | 7/2006 | Van Roey et al. |

FOREIGN PATENT DOCUMENTS

| | | |
|---|---|---|
| JP | 1988/264526 | 11/1988 |
| WO | WO 96/10989 A1 | 9/1996 |
| WO | WO 97/18839 A1 | 5/1997 |
| WO | WO 97/19065 A1 | 5/1997 |

(Continued)

OTHER PUBLICATIONS

Pani et. al. (Antiviral Chemistry and Chemotherapy (2001) 12 (Suppl. 1):51-59).*

(Continued)

*Primary Examiner* — Marcos Sznaidman
(74) *Attorney, Agent, or Firm* — Kirk Baumeister

(57) ABSTRACT

This invention concerns the use of a compound for the manufacture of a medicament for the prevention of HIV infection via sexual intercourse and related intimate contact between partners, wherein the compound is a compound of formula

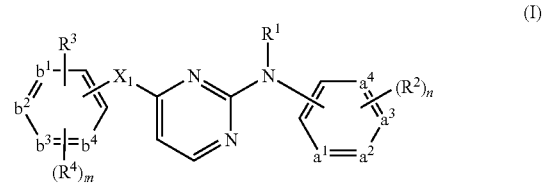

(I)

a N-oxide, a pharmaceutically acceptable addition salt, a quaternary amine and a stereochemically isomeric form thereof, wherein the ring containing $-a^1=a^2-a^3=a^4-$ and $-b^1=b^2-b^3=b^4-$ represents phenyl, pyridyl, pyrimidinyl, pirazinyl, pyridazinyl; n is 0 to 5; m is 1 to 4; $R^1$ is hydrogen; aryl; formyl; $C_{1-6}$alkylcarbonyl; $C_{1-6}$alkyl; $C_{1-6}$alkyloxycarbonyl; substituted $C_{1-6}$alkyl, $C_{1-6}$alkylcarbonyl, $C_{1-6}$alkyloxycarbonyl, $C_{1-6}$alkylcarbonyloxy; substituted $C_{1-6}$alkyloxy$C_{1-6}$alkylcarbonyl; $R^2$ is hydroxy, halo, optionally substituted $C_{1-6}$alkyl, $C_{3-7}$cycloalkyl, optionally substituted $C_{2-6}$alkenyl, optionally substituted $C_{2-6}$alkynyl, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$ or a 5-membered heterocycle; $X_1$ is $-NR^5-$, $-NH-NH-$, $-N=N-$, $-O-$, $-C(=O)-$, $C_{1-4}$alkanediyl, $-CHOH-$, $-S-$, $-S(=O)_p-$, $-X_2-C_{1-4}$alkanediyl- or $-C_{1-4}$alkanediyl-$X_2-$; $R^3$ is $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; substituted $C_{1-6}$alkyl; optionally substituted $C_{1-6}$alkyloxy$C_{1-6}$alkyl; substituted $C_{2-6}$alkenyl; substituted $C_{2-6}$alkynyl; $C_{1-6}$alkyl substituted with hydroxy and a second substituent; $-C(=N-O-R^8)-C_{1-4}$alkyl; $R^7$; or $-X_3-R^7$; $R^4$ is halo, hydroxy, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, $C_{1-6}$alkyloxycarbonyl, $C_{1-6}$alkylcarbonyl, formyl, amino, mono- or di($C_{1-4}$alkyl)amino; and pharmaceutical compositions comprising them.

18 Claims, No Drawings

(56) References Cited

FOREIGN PATENT DOCUMENTS

| WO | WO 98/41512 A1 | | 9/1998 |
|----|----|----|----|
| WO | WO 99/50250 A1 | | 10/1999 |
| WO | WO 00/27825 A1 | | 5/2000 |
| WO | WO 00/62778 A1 | | 10/2000 |
| WO | WO 00/76973 | | 12/2000 |
| WO | WO 00/78731 A1 | | 12/2000 |
| WO | 01/22938 A1 | | 4/2001 |
| WO | WO 01/85700 A2 | | 11/2001 |
| WO | 02/08226 A2 | | 1/2002 |
| WO | 02/070470 A2 | | 9/2002 |
| WO | WO 03/016306 | * | 2/2003 |
| WO | WO 03/016306 A1 | | 2/2003 |
| WO | 03/062238 A1 | | 7/2003 |
| WO | WO 03/094920 | | 11/2003 |
| WO | 2004/050058 A2 | | 6/2004 |
| WO | 2004/069812 A1 | | 8/2004 |

OTHER PUBLICATIONS

Van Herrewege et. al. (AIDS Research and Human Retroviruses (2002) 18:1091-1102).*

Balzarini et. al. (AIDS (1998) 12:1129-1138).*

Ludovici et. al. (Bioorganic and Medicinal Chemistry Letters (2001) 11:2235-2239).*

Jan Balzarini, et al., HIV/AIDS—Intravaginal and Intrarectal Microbicides to Prevent HIV Infection, CMAJ (2005) vol. 4 p. 461-464.

DiFabio, S., et al. "Inhibition of Vaginal Transmission of HIV-1 in hu-SCID Mice by the Non-Nucleoside Reverse Transcriptase Inhibitor TMC120 in a Gel Formulation", AIDS (2003) vol. 17, p. 1597-1604.

Nogradi, M., "Dimethyl-B-Cyclodextrin.", *Drugs of the Future*, 1984, vol. 9, No. 8, pp. 577-578.

Tamiful "Capsules and for Oral Suspension", (2008) p. 1-23.

Tamiflu "Tamiflu for Prevention of Influenza—Protect Family Members", (2006) p. 1-3.

Van Herrewege, Y., t al. "In Vitro Evaluation of Nonnucleoside Reverse Transcriptase Inhibitors UC-781 and TMC120-R147681 as Human Immunodeficiency Virus Micorbicides", Antimicrobial Agents and Chemotherapy, (2004) vol. 48, No. 1 p. 337-339.

International Search Report, for corresponding Application No. PCT/EP04/001011, mailed Jun. 14, 2006.

Ludovici, D.W., et al., "Evolution of Anti-HIV Drug Candidates. Part 3: Diarylpyrimidine (DAPY) Analogues", Bioorganic & Medicinal Chemistry Letters, (2001), vol. 11, pp. 2235-2239.

* cited by examiner

PYRIMIDINE DERIVATIVES FOR THE PREVENTION OF HIV INFECTION

CROSS REFERENCE TO RELATED APPLICATIONS

This application is a continuation of pending U.S. application Ser. No. 10/544,735, filed Aug. 5, 2005, which in turn is a national stage of PCT Application No. PCT/EP2004/001011, filed Feb. 4, 2004, which application claims priority to PCT Application No. PCT/EP2003/001291, filed Feb. 7, 2003, the entire disclosures of which are hereby incorporated in their entirety.

The present invention concerns pyrimidine derivatives for the prevention of HIV infection. In particular, the present invention concerns the use of pyrimidine derivatives for the manufacture of a medicament for the prevention of HIV (Human Immunodeficiency Virus) infection via sexual intercourse and related intimate contact between partners, more in particular the prevention of HIV infection via vaginal sex.

AIDS (acquired Immune Deficiency Syndrome) is the fourth leading cause of death worldwide and the number one cause of death in Africa. There is still no effective treatment or vaccine against AIDS.

Therefore, in order to be able to control the AIDS/HIV epidemic, it is of the utmost importance to prevent the transmission of the HI Virus.

Sexual transmission is the prevalent mode of transmission of HIV. Said sexual HIV transmission is perfectly preventable by consistent and correct condom use. However, despite intensive prevention programs to increase condom use, condoms are still not systematically used, especially in Third World cultures and these cultures are heavily affected by the AIDS/HIV epidemic. Especially in the developing countries, men do not accept condoms, do not like to use them and women often lack the power to determine when, where and how sexual intercourse takes place and therefore are often not in the position to impose the use of condoms.

Therefore, alternatives to condom use for the protection against sexually transmitted infections, especially HIV, are crucial.

An efficacious alternative to condoms are microbicides for topical use. A microbicide is a chemical entity that can prevent or reduce transmission of sexually transmitted infections when applied to the site where the transmission takes place.

Several categories of microbicides have already been evaluated for their use in preventing HIV transmission: products which have a detergent-surfactant like mode of action (e.g. nonoxynol-9), but said products may cause damage to the vaginal epithelium; acid buffers; Lactobacilli; negatively charged natural or synthetic products which interfere with HIV binding to target cells (e.g. sulfated polysaccharides); HIV multiplication inhibiting agents.

The present invention relates to the use of pyrimidine derivatives to prevent HIV infection, to prevent the transmission of HIV infection via sexual intercourse and related intimate contact between partners.

The pyrimidine compounds exhibit HIV replication inhibiting activity in HIV infected warm-blooded animals. They are particularly characterized by an improved ability to inhibit the replication of mutant strains, i.e. strains which have become resistant to art-known drug(s) (drug or multi-drug resistant HIV strains).

Besides their HIV replication inhibiting activity in HIV infected warm-blooded animals, the compounds are also able to prevent the transmission of HIV infection in warm-blooded animals, particularly in humans, via sexual intercourse and related intimate contact between partners. The compounds have the ability to work prophylactic, thus preventing that the warm-blooded animals get infected; they are also able to provide for post-exposure protection, meaning that when the present compounds are applied after the sexual intercourse and related intimate contact between partners has taken place, they are still able to prevent HIV infection. Furthermore, the compounds have little or no immunosuppressive activity at a therapeutic effective dose.

Compounds structurally related to the present compounds are disclosed in the prior art.

WO 99/50250 and WO 00/27825 disclose substituted aminopyrimidines having HIV replication inhibiting properties.

WO 97/19065 discloses substituted 2-anilinopyrimidines useful as protein kinase inhibitors.

WO 00/62778 concerns cyclic protein tyrosine kinase inhibitors.

WO 98/41512 describes substituted 2-anilinopyrimidines useful as protein kinase inhibitors.

U.S. Pat. No. 5,691,364 describes benzamidine derivatives and their use as anti-coagulants.

WO 00/78731 describes 5-cyano-2-aminopyrimidine derivatives as KDR kinase or FGFr kinase inhibitors useful in the prophylaxis and treatment of diseases associated with angiogenesis.

Thus, one aspect of the invention relates to the use of a compound for the manufacture of a medicament for the prevention of HIV infection via sexual intercourse or related intimate contact between partners, wherein the compound has the formula

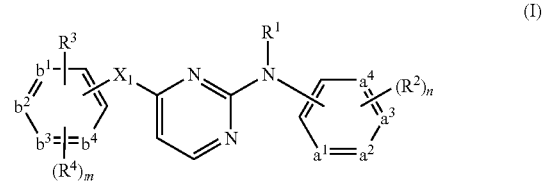

(I)

a N-oxide, a pharmaceutically acceptable addition salt, a quaternary amine or a stereochemically isomeric form thereof, wherein
-$a^1$=$a^2$-$a^3$=$a^4$- represents a bivalent radical of formula

| —CH=CH—CH=CH— | (a-1); |
| —N=CH—CH=CH— | (a-2); |
| —N=CH—N=CH— | (a-3); |
| —N=CH—CH=N— | (a-4); |
| —N=N—CH=CH— | (a-5); |

-$b^1$=$b^2$-$b^3$=$b^4$- represents a bivalent radical of formula

| —CH=CH—CH=CH— | (b-1); |
| —N=CH—CH=CH— | (b-2); |
| —N=CH—N=CH— | (b-3); |
| —N=CH—CH=N— | (b-4); |
| —N=N—CH=CH— | (b-5); | n is 0, 1, 2, 3 or 4; and in case -$a^1$=$a^2$-$a^3$=$a^4$- is (a-1), then n may also be 5;

m is 1, 2, 3 and in case -b$^1$=b$^2$-b$^3$=b$^4$- is (b-1), then m may also be 4;

R$^1$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy; C$_{1-6}$alkyloxyC$_{1-6}$alkylcarbonyl substituted with C$_{1-6}$alkyloxycarbonyl;

each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxycarbonyl, carboxyl, cyano, nitro, amino, mono- or di(C$_{1-6}$alkyl)amino, polyhalomethyl, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

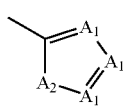
(c)

wherein each A$^1$ independently is N, CH or CR$^6$; and
A$_2$ is NH, O, S or NR$^6$;

X$_1$ is —NR$^5$—, —NH—NH—, —N=N—, —O—, —C(=O)—, C$_{1-4}$alkanediyl, —CHOH—, —S—, —S(=O)$_p$—, —X$_2$—C$_{1-4}$alkanediyl- or —C$_{1-4}$alkanediyl- X$_2$—;

X$_2$ is —NR$^5$—, —NH—NH—, —N=N—, —O—, —C(=O)—, —CHOH—, —S—, —S(=O)$_p$—;

R$^3$ is NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$ and wherein 2 hydrogen atoms bound at the same carbon atom are replaced by C$_{1-4}$alkanediyl; C$_{1-6}$alkyl substituted with hydroxy and a second substituent selected from cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_3$ is —NR$^5$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, —C$_{1-4}$alkanediyl-X$_{2b}$—C$_{1-4}$alkanediyl, —C(=N—OR$^8$)—C$_{1-4}$alkanediyl-;

with X$_{2a}$ being —NH—NH—, —N=N—, —O—, —C(=O)—, —S—, —S(=O)$_p$—; and
with X$_{2b}$ being —NH—NH—, —N=N—, —C(=O)—, —S—, —S(=O)$_p$—;

R$^4$ is halo, hydroxy, C$_{1-16}$alkyl, C$_{3-7}$cycloalkyl, C$_{1-6}$alkyloxy, cyano, nitro, polyhaloC$_{1-6}$alkyl, polyhaloC$_{1-6}$alkyloxy, aminocarbonyl, C$_{1-6}$alkyloxycarbonyl, C$_{1-6}$alkylcarbonyl, formyl, amino, mono- or di(C$_{1-4}$alkyl)amino or R$^7$;

R$^5$ is hydrogen; aryl; formyl; C$_{1-16}$alkylcarbonyl; C$_{1-6}$alkyl; C$_{1-16}$alkyloxycarbonyl; C$_{1-6}$alkyl substituted with formyl, C$_{1-6}$alkylcarbonyl, C$_{1-6}$alkyloxycarbonyl or C$_{1-6}$alkylcarbonyloxy; C$_{1-6}$alkyloxyC$_{1-6}$alkylcarbonyl substituted with C$_{1-6}$alkyloxycarbonyl;

R$^6$ is C$_{1-4}$alkyl, amino, mono- or di(C$_{1-4}$alkyl)amino or polyhaloC$_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkyl;

R$^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$);

R$^8$ is hydrogen, C$_{1-4}$alkyl, aryl or arylC$_{1-4}$alkyl;

R$^9$ and R$^{10}$ each independently are hydrogen; hydroxy; C$_{1-6}$alkyl; C$_{1-6}$alkyloxy; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, R$^7$; or R$^9$ and R$^{10}$ may be taken together to form a bivalent or trivalent radical of formula —CH$_2$—CH$_2$—CH$_2$—CH$_2$— (d-1)

—CH$_2$—CH$_2$—CH$_2$—CH$_2$—CH$_2$— (d-2)

—CH$_2$—CH$_2$—O—CH$_2$—CH$_2$— (d-3)

—CH$_2$—CH$_2$—S—CH$_2$—CH$_2$— (d-4)

—CH$_2$—CH$_2$—NR$^{12}$—CH$_2$—CH$_2$— (d-5)

—CH$_2$—CH=CH—CH$_2$— (d-6)

=CH—CH=CH—CH=CH— (d-7)

R$^{11}$ is cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

$R^{12}$ is hydrogen or $C_{1-4}$alkyl;

$R^{13}$ and $R^{14}$ each independently are $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ is $C_{1-6}$alkyl substituted with cyano or aminocarbonyl;

$R^{16}$ is $C_{1-6}$alkyl optionally substituted with cyano or aminocarbonyl, or $R^7$;

p is 1 or 2;

aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. n-electrons (rule of Huckel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

Whenever used hereinbefore or hereinafter that substituents can be selected each independently out of a list of numerous definitions, such as for example for $R^9$ and $R^{10}$, all possible combinations are intended which are chemically possible and which lead to chemically stable molecules.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhalo$C_{1-4}$alkyl or polyhalo$C_{1-6}$alkyl, they may be the same or different.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (eg. $R^7$, $X_2$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

For some of the compounds of formula (I), their N-oxides, salts, solvates or quaternary amines and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

Pure stereochemically isomeric forms of the present compounds and the intermediates which intervene in the chemical synthesis thereof, can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective or fractional crystallization or chromatographic techniques, e.g. liquid chromatography and the like methods; and finally converting said separated diastereomeric salts or compounds into the corresponding enantiomers, for instance by treatment with alkali. Pure stereochemically isomeric forms may also be obtained from the pure stereochemically isomeric forms of the appropriate intermediates and starting materials, provided that the intervening reactions occur stereospecifically. Preferably if a specific stereoisomer is desired, said compound will be synthesized by stereospecific methods of preparation. These methods will advantageously employ enantiomerically pure starting materials.

An alternative manner of separating the enantiomeric forms of the compounds of formula (I) and intermediates involves liquid chromatography, in particular liquid chromatography using a chiral stationary phase.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

An interesting group of compounds are those compounds of formula (I) wherein $-a^1=a^2-a^3=a^4-$ represents a bivalent radical of formula —CH═CH—CH═CH— (a-1).

Also an interesting group of compounds are those compounds of formula (I) having the formula

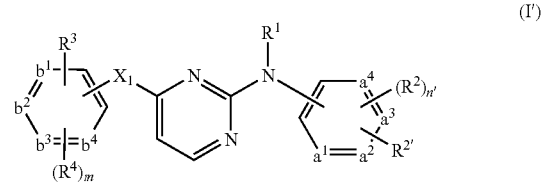

the N-oxides, the pharmaceutically acceptable addition salts, the quaternary amines or the stereochemically isomeric forms thereof, wherein
$-a^1=a^2-a^3=a^4-$, $-b^1=b^2-b^3=b^4-$, $R^1$, $R^2$, $R^3$, $R^4$, m and $X_1$ are as defined hereinabove;
n' is 0, 1, 2 or 3 and in case $-a^1=a^2-a^3=a^4-$ is (a-1), then n' may also be 4;
$R^{2'}$ is halo, $C_{1-6}$alkyl, trihalomethyl, cyano, aminocarbonyl, $C_{1-6}$alkyl substituted with cyano or aminocarbonyl;
provided that $R^{2'}$ is placed at the para position in respect of the $NR^1$ moiety.

Another interesting group of compounds are those compounds of formula (I) having the formula

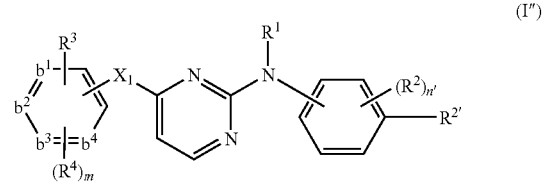

the N-oxides, the pharmaceutically acceptable addition salts, the quaternary amines or the stereochemically isomeric forms thereof, wherein
$-b^1=b^2-b^3=b^4-$, $R^1$, $R^2$, $R^3$, $R^4$, m and $X_1$ are as defined hereinabove;
n' is 0, 1, 2, 3 or 4;
$R^{2'}$ is halo, $C_{1-6}$alkyl, trihalomethyl, cyano, aminocarbonyl, $C_{1-6}$alkyl substituted with cyano or aminocarbonyl.

Yet a further interesting group of compounds are those compounds of formula (I) having the formula

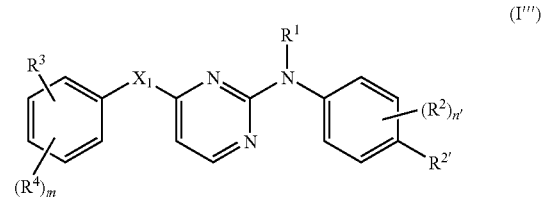

the N-oxides, the pharmaceutically acceptable addition salts, the quaternary amines or the stereochemically isomeric forms thereof, wherein
$R^1$, $R^2$, $R^3$, $R^4$ and $X_1$ are as defined hereinabove;
n' is 0, 1, 2, 3 or 4;
$R^{2'}$ is halo, $C_{1-6}$alkyl, trihalomethyl, cyano, aminocarbonyl, $C_{1-6}$alkyl substituted with cyano or aminocarbonyl.

Also particular compounds are those compounds of formula (I), (I'), (I") or (I''') wherein one or wherever possible more of the following conditions apply:
a) m is 1, 2 or 3, in particular 2 or 3, more in particular 2, even more in particular m is 2 and said two $R^4$ substituents are placed in position 2 and 6 (ortho position) in respect of the $X_1$ moiety;

b) m is 1, 2 or 3 and $R^3$ is placed in position 4 (para position) in respect of the $X_1$ moiety;
c) $X_1$ is —$NR^5$—, —NH—NH—, —N=N—, —O—, —C(=O)—, $C_{1-4}$alkanediyl, —CHOH—, —S(=O)$_p$—, —$X_2$—$C_{1-4}$alkanediyl- or —$C_{1-4}$alkanediyl-$X_2$—;
d) where applicable n' is 0;
e) where applicable n is 1 and said $R^2$ substituent is placed in position 4 (para position) in respect of the $NR^1$-linker;
f) $R^2$ is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p R^6$, —NH—S(=O)$_p R^6$, —NHC(=O)H, —C(=O)NHNH$_2$, —NHC(=O)$R^6$, —C(=NH)$R^6$ or a radical of formula

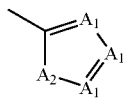

(c)

wherein each $A^1$ independently is N, CH or $CR^6$; and $A_2$ is NH, O, S or $NR^6$;
g) $R^{2'}$ is halo, $C_{1-6}$alkyl, trihalomethyl, cyano, $C_{1-6}$alkyl substituted with cyano or aminocarbonyl;
h) $R^2$ is cyano, aminocarbonyl or $C_{1-6}$alkyl substituted with cyano or aminocarbonyl, in particular cyano;
i) $R^{2'}$ is cyano, aminocarbonyl or $C_{1-6}$alkyl substituted with cyano or aminocarbonyl, in particular cyano.

A preferred embodiment of the present compounds encompasses those compounds of formula (I), (I'), (I'') or (I''') wherein $R^3$ is $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{2-6}$alkyl substituted with cyano or aminocarbonyl; $C_{1-6}$alkyl substituted with $NR^9R^{10}$, —C(=O)—$NR^{9a}R^{10}$, —C(=O)—$C_{1-6}$alkyl or $R^7$; $C_{1-6}$alkyl substituted with two or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$ and wherein 2 hydrogen atoms bound at the same carbon atom are replaced by $C^{1-4}$alkanediyl; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$; with $R^{9a}$ representing hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl, —CH(=$NR^{11}$) or $R^7$, wherein each of the aforementioned $C_{1-6}$alkyl groups in the definition of $R^{9a}$ may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(=O)$_p R^6$, —NH—S(=O)$R^6$, —C(=O)$R^6$, —NHC(=O)H, —C(=O)NHNH$_2$, —NHC(=O)$R^6$, —C(=NH)$R^6$, $R^7$; $R^{9a}$ may also be taken together with $R^{10}$ to form a bivalent or trivalent radical of formula (d-1), (d-2), (d-3), (d-4), (d-5), (d-6) or (d-7) as defined hereinabove.

A further interesting group of compounds are those compounds of formula (I), (I'), (I'') or (I''') wherein $R^3$ is $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with $NR^9R^{10}$, —C(=O)—$NR^{9a}R^{10}$, —C(=O)—$C_{1-6}$alkyl or $R^7$; $C_{1-6}$alkyl substituted with two or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, Also an interesting group of compounds are those compounds of formula (I), (I'), (I'') or (I''') wherein $R^3$ is —CH=N—NH—C(=O)—$R^{16}$; $C_{1-6}$alkyl substituted with $NR^9R^{10}$, —C(=O)—$NR^{9a}R^{10}$, —C(=O)—$C_{1-6}$alkyl or $R^7$; $C_{1-6}$alkyl substituted with two or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$; with R$^{9a}$ as defined hereinabove.

Another interesting group of compounds are those compounds of formula (I), (I'), (I") or (I''') wherein R$^3$ is NHR$^{13}$, NR$^{13}$R$^{14}$, —C(=O)—R$^{15}$, C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$ and wherein 2 hydrogen atoms bound at the same carbon atom are replaced by C$_{1-4}$alkanediyl; C$_{1-6}$alkyl substituted with hydroxy and a second substituent selected from cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$.

Also interesting are those compounds of formula (I), (I'), (I") or (I''') wherein R$^3$ is C$_{1-6}$alkyl substituted with NR$^9$R$^{10}$, —C(=O)—NR$^{9a}$R$^{10}$, —C(=O)—C$_{1-6}$alkyl or R$^7$; C$_{1-6}$alkyl substituted with two or more substituents each independently selected from cyano, NR$^9$R$^{10}$, —C(=O)—NR$^9$R$^{10}$, —C(=O)—C$_{1-6}$alkyl or R$^7$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$ and wherein 2 hydrogen atoms bound at the same carbon atom are replaced by C$_{1-4}$alkanediyl; C$_{1-6}$alkyl substituted with hydroxy and a second substituent selected from cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$; with R$^{9a}$ as defined hereinabove.

Also interesting are those compounds of formula (I), (I'), (I") or (I''') wherein R$^3$ is C$_{1-6}$alkyl substituted with one or more substituents each independently selected from cyano, NR$^9$R$^{10}$ or R$^7$; C$_{2-6}$alkenyl substituted with one or more substituents each independently selected from cyano, NR$^9$R$^{10}$ or R$^7$; C$_{1-6}$alkyloxyC$_{1-6}$alkyl substituted with cyano; C$_{1-6}$alkyl substituted with hydroxy and a second substituent selected from cyano or R$^7$; —C(=N—O—R$^8$)—C$_{1-4}$alkyl; R$^7$ or —X$_3$—R$^7$.

Another interesting group of compounds are those compounds of formula (I), (I'), (I") or (I''') wherein R$^3$ is R$^7$.

Still another interesting group of compounds are those compounds of formula (I), (I'), (I") or (I''') wherein R$^3$ is C$_{1-6}$alkyl substituted with cyano, in particular C$_{2-6}$alkyl substituted with cyano, more in particular ethyl or propyl substituted with cyano; or C$_{2-6}$alkenyl substituted with cyano. Preferred is C$_{2-6}$alkenyl substituted with cyano.

Also an interesting group of compounds are those compounds of formula (I), (I'), (I") or (I''') wherein R$^3$ is C$_{1-6}$alkyl substituted with cyano and R$^7$, or C$_{2-6}$alkenyl substituted with cyano and R$^7$.

A further interesting group of compounds are those compounds of formula (I), (I'), (I") or (I''') wherein R$^3$ is C$_{1-6}$alkyl substituted with R$^7$.

Still a further interesting group of compounds are those compounds of formula (I), (I'), (I") or (I''') wherein R$^3$ is —C(=N—O—R$^8$)—C$_{1-4}$alkyl.

Also an interesting group of compounds are those compounds of formula (I), (I'), (I") or (I''') wherein R$^3$ is C$_{1-6}$alkyl substituted with hydroxy and a second substituent selected from cyano or R$^7$.

Also an interesting group of compounds are those compounds of formula (I), (I'), (I") or (I''') wherein R$^2$ or R$^{2'}$ is cyano or aminocarbonyl and R$^1$ is hydrogen.

Another interesting group of compounds are those compounds of formula (I), (I'), (I") or (I''') wherein m is 2 or 3 and X$_1$ is —NR$^5$—, —O—, —C(=O)—, —CH$_2$—, —CHOH—, —S—, —S(=O)$_p$—, in particular wherein X$_1$ is —NR$^5$—, or —O—.

Also an interesting group of compounds are those compounds of formula (I), (I'), (I") or (I''') wherein one or more, preferably all of the following restrictions apply
a) n is at least 1, in particular 1; or n' is 0;
b) R$^2$ or R$^{2'}$ is cyano;
c) m is 1, 2 or 3;
d) R$^4$ is C$_{1-6}$alkyl, especially methyl; nitro; amino; halo; C$_{1-6}$alkyloxy or R$^7$;
e) R$^3$ is R$^7$, NR$^{13}$R$^{14}$, —C(=O)R$^{15}$, —CH=N—NH—C(=O)R$^{16}$, —C(=O)NHR$^{13}$, —C(=O)NR$^{13}$R$^{14}$, —C(=N—OR$^8$)—C$_{1-4}$alkyl, C$_{1-6}$alkyl substituted with cyano, C$_{1-6}$alkyl substituted twice with cyano, C$_{1-6}$alkyl substituted with NR$^9$R$^{10}$, C$_{1-6}$alkyl substituted with hydroxy and cyano, C$_{1-6}$alkyl substituted with hydroxy and R$^7$, C$_{1-6}$alkyloxy C$_{1-6}$alkyl, C$_{1-6}$alkyloxy C$_{1-6}$alkyl substituted with cyano, C$_{2-6}$alkenyl substituted with R$^7$, C$_{2-6}$alkenyl substituted with cyano, C$_{2-6}$alkenyl substituted twice with cyano, C$_{2-6}$alkenyl substituted with cyano and R$^7$, C$_{2-6}$alkenyl substituted with cyano and —C(=O)—C$_{1-6}$alkyl, C$_{2-6}$alkenyl substituted with cyano and halo, C$_{2-6}$alkenyl substituted with —C(=O)—NR$^9$R$^{10}$, C$_{2-6}$alkenyl substituted with halo, C$_{2-6}$alkenyl substituted twice with halo or C$_{2-6}$alkenyl substituted with NR$^9$R$^{10}$;
f) X$_3$ is —C(=O)—, —CH$_2$—C(=O)—, or —C(=N—OR$^8$)—C$_{1-4}$alkanediyl-;
g) X$_1$ is NH or O;
h) R$^1$ is hydrogen or C$_{1-4}$alkyl.

Preferred compounds of formula (I), (I'), (I") or (I''') are compounds 1, 25, 84, 133, 152, 179, 233, 239, 247, 248, 255 (see Tables 1, 2 and 3), their N-oxides, pharmaceutically acceptable addition salts, quaternary amines and stereochemically isomeric forms thereof.

The compounds of formula (I) are disclosed in WO 2003/016306. Their preparation is also described therein. Some of the intermediates and starting materials are known compounds and may be commercially available or may be prepared according to art-known procedures or some of the compounds of formula (I) or the described intermediates may be prepared according to the procedures described in WO 99/50250 and WO 00/27825.

The present invention also relates to a novel compound, i.e. 4-[[4-[4-(2-cyanoethenyl)-2,6-dimethylphenoxy]-2-pyrimidinyl]amino]benzonitrile (E) (compound 255); a N-oxide, a pharmaceutically acceptable addition salt, a quaternary amine or a stereochemically isomeric from thereof.

Said novel compound can be prepared as follows:

a) NaH (60%) (0.0233 mol) was added to a mixture of 4-hydroxy-3,5-dimethyl benzaldehyde (0.0233 mol) in dioxane (35 ml) under $N_2$ flow. The mixture was stirred for 5 minutes. 1-methyl-2-pyrrolidinone (35 ml) was added. The mixture was stirred for 10 minutes. 4-[(4-chloro-2-pyrimidinyl)amino]benzonitrile (0.0212 mol) was added. The mixture was stirred at 155° C. for 12 hours, poured out into $H_2O$ and extracted with $CH_2Cl_2$. The organic layer was separated, washed several times with $H_2O$, dried ($MgSO_4$), filtered and the solvent was evaporated. The residue was purified with column chromatography over silica gel (eluent: $CH_2Cl_2$ 100; 35-70 μm). The pure fractions were collected and the solvent was evaporated. The obtained fraction was crystallized from $CH_3CN$/diisopropyl ether. The precipitate was filtered off and dried, yielding 2.2 g of intermediate 1.

b) Potassium tert.-butoxide (0.0065 mol) was added portionwise at 5° C. to a mixture of cyanomethyl phosphonic acid diethylester (0.0065 mol) in tetrahydrofuran (20 ml) under $N_2$ flow. The mixture was stirred at room temperature for 1 hour. A solution of intermediate 1 (0.0044 mol) in tetrahydrofuran (20 ml) was added. The mixture was stirred for 2 hours at room temperature. The mixture was extracted with $CH_2Cl_2$. The organic layer was separated, dried ($MgSO_4$), filtered and the solvent was evaporated. The residue (1.8 g) was crystallized from diethyl ether. The precipitate was filtered off and dried. The residue (1.5 g) was purified by column chromatography over kromasil (eluent: CH3CN/ $AcNH_4$ 50/50; 10 μm). Two fractions (F1, F2) were collected and the solvent was evaporated. Yield: 0.47 g of F1 and 0.44 g of F2. Ft was crystallized from diisopropyl ether. The precipitate was filtered off and dried, yielding 0.4 g of 4-[[4-[4-(2-cyanoethenyl)-2,6-dimethylphenoxy]-2-pyrimidinyl]amino]benzonitrile (E) (compound 255).

As already indicated above, the compounds of formula (I), (I'), (I''), (I''') show antiretroviral properties (reverse transcriptase inhibiting properties) in HIV infected warm-blooded animals, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV. The HIV replication inhibiting effect of the compounds of formula (I) is described in WO 2003/016306. Compound 255 has a $pIC_{50}$ value of 9.00 when tested in the test described under the heading "C. Pharmacological example" of WO 2003/016306.

It has now been found that the compounds of formula (I) can not only be used to treat HIV infected warm-blooded animals, but that they can also be used to prevent that warm-blooded animals, including humans, get HIV infected via sexual intercourse or related intimate contact between partners. Thus, as already indicated above, the present invention relates to the use of a compound of formula (I) for the manufacture of a medicament for the prevention of HIV infection via sexual intercourse or related intimate contact between partners, in particular to prevent HIV-1 infection and further in particular to prevent HIV or HIV-1 infection with (multi) drug resistant HIV strains, i.e. HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors.

The invention also relates to a method of preventing HIV infection via sexual intercourse or related intimate contact between partners comprising administering to a subject in need thereof an effective amount of a compound of formula (I).

The term sexual intercourse or related intimate contact between partners comprises vaginal sex, anal sex, oral sex and contact of body sites with HIV infected fluids of the sexual partner, in particular semen. Particularly, the term sexual intercourse or related intimate contact between partners constitutes vaginal, anal or oral sex, more particularly vaginal sex.

The contact sites believed to be most responsible for the transmission of HIV via sexual intercourse or related intimate contact between partners are the genitals, rectum, mouth, hands, lower abdomen, upper thighs.

The term "partners" as mentioned hereinbefore or hereinafter defines two or more warm-blooded animals, in particular humans, who are sexually active with each other, ie. who have sexual intercourse with each other or who have intimate contact with each other related to sexual activities.

The present invention also relates to a pharmaceutical composition comprising a pharmaceutically acceptable carrier and as active ingredient a therapeutically effective amount of a compound of formula (I) characterized in that the composition is in a form adapted to be applied to the site where the sexual intercourse or related intimate contact takes place, such as the genitals, rectum, mouth, hands, lower abdomen, upper thighs, especially the vagina and mouth.

As appropriate compositions there may be cited all compositions usually employed for being applied to the vagina, rectum, mouth and skin such as for example gels, jellies, creams, ointments, films, sponges, foams, intravaginal rings, cervical caps, suppositories for rectal or vaginal application, vaginal or rectal or buccal tablets, mouthwashes.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of administration. For example, in preparing the compositions for topical oral administration, any of the usual pharmaceutical media may be employed such as, for example, water, glycols, oils, alcohols and the like in the case of oral liquid preparations such as mouthwashes in the form of a suspension, emulsions and solutions; or solid carriers such as starches, sugars, kaolin, diluents, lubricants, binders, disintegrating agents and the like in the case of tablets. Also included are solid form preparations which are intended to be converted, shortly before use, to liquid form preparations. In the compositions suitable for cutaneous administration, the carrier optionally comprises a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a cream or gel.

In order to increase the residence time of the pharmaceutical composition at the site of administration, it may be advantageous to include in the compositions of the present invention a bioadhesive, in particular a bioadhesive polymer. A bioadhesive may be defined as a material that adheres to a live biological surface such as for example a mucus membrane or skin tissue. The term bioadhesive is well-known to the person skilled in the art. Thus, the present invention also relates to a pharmaceutical composition comprising a pharmaceutically acceptable carrier and as active ingredient a therapeutically effective amount of a compound of formula (I) characterized in that the pharmaceutical composition is bioadhesive to the site of application. Preferably, the site of application is the vagina, rectum, mouth or skin, most preferred is the vagina.

Examples of bioadhesives which may be used in the pharmaceutical compositions of the present invention comprise polyacrylic acid derivatives, such as for example carbopol or polycarbophil, e.g. carbopol 934P, carbopol 940, polycarbophil AA1; cellulose ether derivatives such as for example hydroxypropyl methylcellulose, hydroxypropyl cellulose, hydroxyethyl cellulose, sodium carboxymethyl cellulose, chitosan; natural polymers such as for example alginates, tragacanth, inulin; pregelatinized starch.

An embodiment of the present invention relates to a gel containing carbopol, hydroxypropyl cellulose, hydroxyethyl cellulose or pregelatinized starch.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infra-red spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

The compounds of formula (f) may be formulated in the pharmaceutical compositions of the present invention in the form of particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in case the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer, b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into the pharmaceutical dosage forms of the present invention.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

Those of skill in the prevention of HIV-infection could determine the effective daily amount from the test results presented here. The exact dosage depends on the particular compound of formula (I) used.

In order to provide for an increased protection against HIV infection the compounds of formula (I) can also be combined with another or other antiretrovirals. Thus, the present invention also provides for a pharmaceutical composition according to the invention comprising a compound of formula (I) and further comprising one or more additional antiretroviral compounds. The present invention also relates to a product containing (a) a compound of formula (I), and (b) one or more additional antiretroviral compounds, as a combined preparation for simultaneous, separate or sequential use in HIV infection prevention. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-dihydro-4-methyl-6H-dipyrido-[3,2-b: 2',3'-e][1,4]diazepin-6-one), efavirenz, delavirdine, TMC-120, TMC-125 and the like; phosphonate reverse transcriptase inhibitors, e.g. tenofovir and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the prophylactic effect of these compounds can be potentiated. Combination therapies as described above may exert a synergistic effect in inhibiting HIV replication because each component of the combination acts on a different site of HIV replication. The use of such combinations may reduce the dosage of a given conventional anti-retroviral agent which would be required for a desired prophylactic effect as compared to when that agent is administered as a monotherapy. These combinations reduce potential of resistance to single agent therapies, while minimizing any associated toxicity. These combinations may also increase the efficacy of the conventional agent without increasing the associated toxicity.

In addition to the above-described combination of the present compounds with another or other antiretrovirals, the compounds of the present invention may also be administered in combination with art-known microbicides. They can block the infection by creating a barrier between the pathogen, in this case the Human Immunodeficiency Virus, and the site at which transmission will take place, e.g. the vagina; they can kill or immobilize the pathogen; they can prevent a virus from replicating once it has infected the cells that line the site of transmission, e.g. the cells that line the vaginal wall. Examples of microbicides are a) antibodies. Scientists have found ways to isolate antibodies that counteract HIV and to mass-produce them. Therefore, these HIV antibodies can be combined with the present compounds of formula (I) to prevent HIV infection.
b) Detergents and surfactants. These compounds are able to disrupt the outer shell of viruses and therefore are useful as microbicide and they can be combined with the present compounds of formula (I) to prevent HIV infection. Examples of such detergents and surfactants are nonoxynol-9 and octoxynol-9, but all detergents and surfactants that are commonly used in shampoos, toothpastes and cleaning solutions, contact lens solutions are equally suitable.
c) Coatings for the site of transmission, i.e. coatings for the site of administration of the pharmaceutical composition, such as for example gels. These products may prevent HIV from entering the cells lining the site of transmission, e.g. the vaginal lining. Examples are sulphated and sulphonated polymers such as PC-515 (carrageenan), Pro-2000, dextrin 2 sulphate.
d) Peptides. Peptides are small protein molecules that line every surface of the body, e.g. skin, tongue, intestinal tract, and they may kill pathogens within minutes of contact. Thus, if applied at the site of potential transmission of HIV, peptides may kill off the pathogens before they cause infection.
e) pH regulators, especially for the vagina. These compounds regulate the natural acidity of the vagina making it inhospitable for the HIV. The natural vaginal environment is too acidic for HIV to survive, but semen is alkaline and the vagina becomes more alkaline during intercourse, allowing HIV to survive. By administering pH regulating compounds the alkaline environment that is created by semen can be countered. PH regulators encompass the use of Lactobacillus bacteria that produce hydrogen peroxide and thereby help to keep the vaginal environment healthy and acidic.

In the compositions of the present invention, one or more or all of the above-listed categories of microbicides may be combined with a compound of formula (I). Thus, the present invention also relates to a pharmaceutical composition according to the invention comprising a compound of formula (I) and further comprising one or more components wherein the components are selected from antibodies, detergents or surfactants, coatings for the site of administration of the pharmaceutical composition, peptides, pH regulators. The present invention also relates to a product containing (a) a compound of formula (I), and (b) one or more components selected from antibodies, detergents or surfactants, coatings for the site of administration of the pharmaceutical composition, peptides, pH regulators, as a combined preparation for simultaneous, separate or sequential use in HIV infection prevention. The different drugs may be combined in a single preparation together with pharmaceutically acceptable carriers.

The present invention relates also to a pharmaceutical composition as outlined hereinabove further comprising a spermicidal compound. Said compositions are able to prevent at the same time conception and HIV infection. Suitable spermicides are for example nonoxynol-9, octoxynol-9, menfegol, benzalkonium chloride, N-docasanol.

Although the present invention focuses on the use of the present compounds for preventing HIV infection via sexual intercourse or related intimate contact between partners, the present compounds may also be used as inhibitory agents for the prevention of infections caused by other viruses which depend on similar reverse transcriptases for obligatory events in their life cycle.

The following Tables 1, 2 and 3 list compounds of formula (I).

TABLE 1

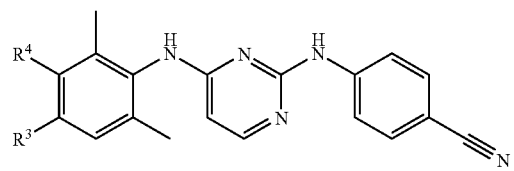

| Comp No. | R³ | R⁴ | Physical data mp. °C./ (MH+)* |
|---|---|---|---|
| 2 | 2-benzofuranyl | H | mp. > 240 |
| 21 | 3-thienyl | H | mp. 220 |
| 3 | 2-furanyl | H | mp. 228 |
| 28 | 2-thienyl | H | mp. 235 |
| 29 | phenyl | H | mp. 230 |
| 1 | —CH═CH—CN | H | mp. 245, (E) |

TABLE 1-continued

| Comp No. | R³ | R⁴ | Physical data mp. °C./(MH+)* |
|---|---|---|---|
| 30 | 2,4-dichlorophenyl | H | (460) |
| 31 | 2-benzo[b]thienyl | H | (448) |
| 32 | 1-naphthalenyl | H | (442) |
| 33 | 3-chlorophenyl | H | (426) |
| 34 | 3-acetylphenyl | H | (434) |
| 35 | 3-methylphenyl | H | (406) |
| 36 | 2-naphthalenyl | H | (442) |
| 37 | 4-chlorophenyl | H | (426) |
| 38 | 4-methoxyphenyl | H | (422) |
| 39 | 4-methylthiophenyl | H | (438) |
| 40 | 4-(hydroxymethyl)phenyl | H | |
| 19 | benzoyl | H | mp. 220 |
| 8 | —C(=N—OH)—CH(CH₃)₂ | H | mp. 156 |
| 20 | α-hydroxybenzyl | H | mp. 205 |
| 27 | phenacyl (—CH₂—C(=O)—Ph, attached via C=O) | H | mp. 193 |
| 41 | 2-hydroxy-2-phenylethyl | H | mp. 200 |
| 42 | —C(=N—OH)—CH₂—Ph | H | mp. 155 |
| 43 | —CH₂-piperidin-1-yl | H | mp. 110 |
| 44 | —C(=N—O—CH₃)—CH₂—Ph | H | mp. 110 |
| 45 | —C(=N—OH)—CH₃ | H | mp. 135 |
| 9 | —C(=N—O—CH₃)—CH(CH₃)₂ | H | mp. 185 |

TABLE 1-continued

| Comp No. | R³ | R⁴ | Physical data mp. °C./(MH+)* |
|---|---|---|---|
| 46 | (isopropyl C=N-O-CH₂-phenyl oxime) | H | mp. 164 |
| 47 | —CH₂—N(CH₂—CH₃)₂ | H | mp. 150 |
| 48 | —CH₂-morpholinyl | H | mp. 85 |
| 15 | —CH=C(CN)-(4-fluorophenyl) | H | (461) |
| 49 | —CH=C(CN)-(2-thienyl) | H | (449) |
| 50 | —CH=C(CN)-(benzo[1,3]dioxol-5-yl) | H | (487) |
| 51 | —CH=C(CN)-(2-naphthyl) | H | (493) |
| 52 | —CH=C(CN)-(4-methoxyphenyl) | H | (473) |
| 53 | —CH=C(CN)-phenyl | H | (443) |
| 54 | —CH=C(CN)-(1-methyl-1H-pyrrol-2-yl) | H | (446) |

TABLE 1-continued
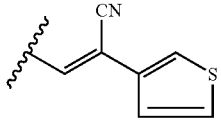
| Comp No. | R³ | R⁴ | Physical data mp. ° C./ (MH+)* |
|---|---|---|---|
| 55 | 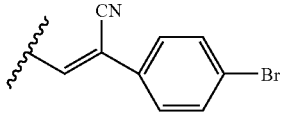 [SMILES: */C=C(\C#N)c1ccc(Br)cc1] | H | (449) |
| 56 | 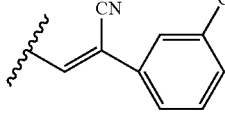 | H | (521) |
| 57 | 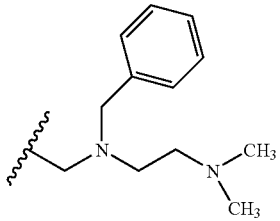 | H | (457) |
| 6 | —CH₂—N(CH₃)—CH₂—CH₂—N(CH₃)₂ | H | (430) |
| 58 | 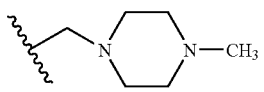 [SMILES: *CN1CCN(C)CC1] | H | (506) |
| 59 | 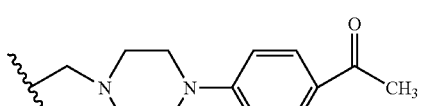 | H | (428) |
| 60 | 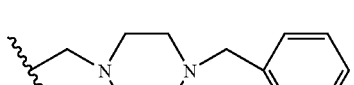 | H | (532) |
| 61 |  | H | (504) |
| 62 | 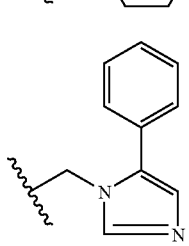 | H | (503) |
| 63 | | H | (472) |

TABLE 1-continued

[Structure: R⁴ and R³ substituted phenyl connected via NH to pyrimidine, then NH to 4-cyanophenyl; phenyl bearing R³/R⁴ has two methyl groups ortho to NH]

| Comp No. | R³ | R⁴ | Physical data mp. ° C./ (MH+)* |
|---|---|---|---|
| 64 | -CH₂-piperazine-N-(2-pyridyl) | H | (491) |
| 65 | —CH₂—N(CH₃)—CH₂—CH₂—CH₂—CH₃ | H | (415) |
| 66 | -CH₂-(4-methyl-1,4-diazepan-1-yl) | H | (442) |
| 67 | -CH₂-(5-methylimidazol-1-yl) | H | (410) |
| 68 | —CH₂—N(CH₃)—CH₂—CH₂—CH₃ | H | (401) |
| 69 | -CH₂-pyrrolidin-1-yl | H | (399) |
| 70 | -CH₂-imidazol-1-yl | H | (396) |
| 71 | —CH₂—N(CH₂—CH₂—O—CH₃)₂ | H | (461) |
| 72 | -CH₂-(3-ethoxycarbonylpiperidin-1-yl) | H | (485) |
| 73 | -CH₂-N(CH₃)-(1-methylpiperidin-4-yl) | H | (456) |
| 74 | -CH₂-piperazine-N-(2-pyrimidinyl) | H | (492) |
| 75 | —CH₂—N(CH₃)—CH₂—CH₂—CN | H | (412) |
| 76 | -CH₂-(2,6-dimethylmorpholin-4-yl) | H | (443) |

TABLE 1-continued

| Comp No. | R³ | R⁴ | Physical data mp. °C./ (MH+)* |
|---|---|---|---|
| 77 | (CH₂-pyrrole) | H | (397) |
| 78 | (CH₂-thiazolidine) | H | (417) |
| 79 | (CH₂-N(Et)-CH₂-pyridyl) | H | (464) |
| 80 | —CH₂—NH—CH₂—CH₂—N(CH₂—CH₃)₂ | H | mp. 105 |
| 81 | (C(=O)-furan-2-yl) | H | mp. 240 |
| 82 | (CH(OH)-furan-2-yl) | H | mp. 170 |
| 24 | —CH₂—CH₂—CN | H | mp. 208 |
| 83 | (3-phenyl-1,2,4-oxadiazol-5-yl) | H | mp. > 250° C. |
| 14 | (2-(furan-2-yl)-acrylonitrile) | H | mp. 158 |
| 84 | —C(CH₃)=CH—CN | H | mp. 224° C. (E) |
| 18 | —CH(OH)—CH₂—CN | H | mp. 252° C. |
| 85 | (CH₂-(2-bromoimidazol-1-yl)) | H | (474) |
| 86 | (CH₂-(3-phenyl-1,2,4-triazol-1-yl)) | H | (473) |

TABLE 1-continued

| Comp No. | R³ | R⁴ | Physical data mp. °C./ (MH+)* |
|---|---|---|---|
| 87 | -CH₂-(1H-imidazol-1-yl with 5-CH₂OH) | H | (426) |
| 88 | -CH₂-(1H-imidazol-1-yl with 2-CH₃) | H | (424) |
| 89 | -CH₂-(1H-imidazol-1-yl with 4,5-diCN) | H | (446) |
| 90 | -CH₂-(1H-1,2,3-triazol-1-yl) | H | (397) |
| 91 | -CH₂-(1H-imidazol-1-yl with 2-isopropyl) | H | (438) |
| 92 | -CH₂-(1H-imidazol-1-yl with 2-propyl) | H | (438) |
| 93 | -CH₂-(1H-imidazol-1-yl with 2-CH₃) | H | (410) |
| 94 | -CH₂-(1H-pyrazol-1-yl with 3-CH₃) | H | (410) |
| 95 | -CH₂-(1H-imidazol-1-yl with 2-CH₃, 4,5-diCl) | H | (478) |

TABLE 1-continued

[Structure: R⁴ and R³ substituted benzene with methyl groups, NH linked to pyrimidine, which is NH linked to 4-cyanophenyl]

| Comp No. | R³ | R⁴ | Physical data mp. °C./ (MH+)* |
|---|---|---|---|
| 96 | [2-(pyridin-4-yl)-imidazol-1-yl]methyl | H | (473) |
| 103 | —CH═C(CH₃)—CN | H | mp. 201° C. (E) |
| 11 | —CH═C(CH₃)—CN | H | mp. 246° C. (Z) |
| 10 | —CH═CH—CN | H | mp. 258° C. (Z) |
| 4 | —CH₂—CN | H | |
| 17 | 3-((dimethylamino)methyl)-1,2,4-oxadiazol-5-yl | H | mp. 110° C. |
| 97 | 3-ethyl-1,2,4-oxadiazol-5-yl | H | mp. 240° C. |
| 16 | 2-mercapto-1,3,4-oxadiazol-5-yl | H | mp. > 250° C. |
| 7 | —CH₂—O—CH₂—CH₂—CN | H | mp > 260 |
| 5 | 4-thiomorpholinyl | —NO₂ | mp. 268 |
| 98 | 4-morpholinyl | —NO₂ | mp. 210 |
| 22 | 1-piperidinyl | —NO₂ | mp. 252 |
| 23 | 1-piperidinyl | —NH₂ | mp. 262 |
| 12 | H | —C(CH₃)═CH—CN (E) | (381) |
| 13 | H | —C(CH₃)═CH—CN (Z) | (381) |
| 127 | —N(CH₃)₂ | H | mp. 228° C. |
| 123 | —C(═O)—CH₂—CN | H | mp. 150° C. |
| 116 | isonicotinoyl hydrazone | H | (463) |
| 128 | 3-fluorobenzoyl hydrazone | H | (480) |
| 129 | furan-2-carbonyl hydrazone | H | (452) |

TABLE 1-continued

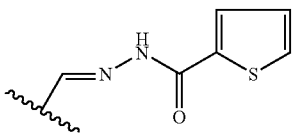 [SMILES: */C=N/NC(=O)c1cccs1]

| Comp No. | R³ | R⁴ | Physical data mp. ° C./ (MH+)* |
|---|---|---|---|
| 130 | —CH=N—NH—C(=O)—CH₃ | H | (400) |
| 131 | —CH=N—NH—C(=O)—CH₂—CN | H | (425) |
| 132 | 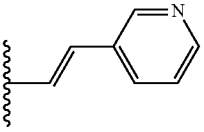 [SMILES: */C=C/c1cccnc1] | H | (468) |
| 115 | —C(=O)—NH—CH₃ | H | (373) |
| 134 | —C(=O)—N(CH₃)₂ | H | (387) |
| 135 | —C(=O)—N(CH₃)—CH₂—CH₃ | H | (401) |
| 136 | —C(=O)—N(CH₂—CH₃)₂ | H | (415) |
| 137 | —C(=O)—NH—CH₂—CH₃ | H | (387) |
| 138 | —C(=O)—NH—CH₂—CN | H | (398) |
| 139 | —C(=O)—N(CH₃)—CH₂—CN | H | (412) |
| 140 | —C(=O)—NH—CH₂—C≡CH | H | (397) |
| 141 | —C(=O)—NH—CH₂—CH=CH₂ | H | (399) |
| 142 | —C(=O)—NH—CH(CH₃)₂ | H | (401) |
| 143 | —N[CH₂—CH(CH₃)₂]₂ | H | mp. 238° C. |
| 144 | —CH₂—CH(CN)₂ | H | mp. 160° C. |
| 106 | —CH=C(CN)—C(=O)—C(CH₃)₃ | H | (E), mp. 193° C. |
| 145 | 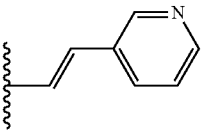 [SMILES: */C=C/c1cccnc1] | H | (E), mp. 229° C. |
| 146 | 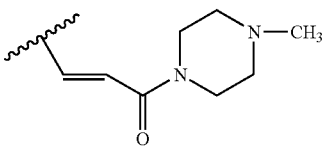 [SMILES: */C=C/C(=O)N1CCN(C)CC1] | H | (Z), mp. 258° C. |
| 147 | —CH=C(CN)—CH₂—CN | H | (Z/E = 88/12) (406) |
| 148 | —C(CH₂—CH₃)=CH—CN | H | (E), mp. 173° C. |
| 149 | —C(CH(CH₃)₂)=CH—CN | H | (E), mp. 132° C. |
| 150 | —C(CH(CH₃)₂)=CH—CN | H | (Z), mp. 132° C. |
| 151 | —CH=C(CH₃)—CN | H | (Z), mp. 246° C. |
| 152 | —CH=C(CH₃)—CN | H | (E), mp. 201° C. |
| 153 | —CH₂—CH(CH₃)—CN | H | mp. 187° C. |
| 124 | —C(Cl)=CH—CN | H | |
| 154 | —CH=CH—C(=O)—N(CH₃)—CH₂—CN | H | (E) |
| 112 | —CH=CH—C(=O)—N(CH₃)₂ | H | (E), mp. > 264° C. |
| 155 | 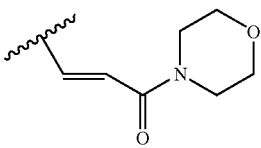 [SMILES: */C=C/C(=O)N1CCOCC1] | H | (E), mp. 156° C. |
| 156 |  | H | (E), mp. 168° C. |

TABLE 1-continued

| Comp No. | R³ | R⁴ | Physical data mp. °C./ (MH+)* |
|---|---|---|---|
| 157 | (piperidinyl-C(=O)-CH=CH-) | H | (E), mp. > 265° C. |
| 158 | —CH=CH—C(=O)—N(CH₃)—CH₂—CH₃ | H | (E), mp. > 260° C. |
| 114 | —CH=CH—C(=O)—N(CH₃)—(CH₂)₂—CN | H | (E), mp. 168° C. |
| 159 | —CH=CH—C(=O)—N(CH₂—CH₃)₂ | H | (E), mp. 249° C. |
| 160 | —C(CH₃)=C(CH₃)—CN | H | (E) |
| 107 | —CH=CH—Cl | H | (Z), mp. 250° C. |
| 161 | —CH=CH—Br | H | (Z), mp. 248° C. |
| 111 | —CH=C(Br)₂ | H | mp. 223° C. |
| 122 | (2-pyridyl-CH=CH-) | H | (E), mp. 120° C. |
| 162 | (4-pyridyl-CH=CH-) | H | (E), mp. > 260° C. |
| 163 | (4-pyridyl-CH=CH-) | H | mp. 128° C. |
| 164 | (2-furyl-CH=CH-) | H | mp. 104° C. |
| 125 | (5-(HON=CH)-furan-2-yl-) | H | |
| 104 | (5-(O=CH)-furan-2-yl-) | H | |
| 165 | (2-thienyl-CH=CH-) | H | mp. 112° C. |

TABLE 1-continued

[Structure: R4 and R3 substituted dimethylphenyl-NH-pyrimidine-NH-phenyl-CN]

| Comp No. | R³ | R⁴ | Physical data mp. °C./(MH+)* |
|---|---|---|---|
| 166 | [1-methylpyrrol-2-yl vinyl] | H | mp. 194° C. |
| 167 | [4-cyanophenyl vinyl] | H | mp. 191° C. |
| 126 | [5-cyanofuran-2-yl] | H | mp. > 260° C. |
| 168 | —CH₂—O—CH₂—CH₃ | H | mp. 201 ° C. |
| 117 | H | —N(CH₃)₂ | mp. 132° C. |
| 120 | —CH=C(CN)₂ | H | |
| 253 | —CH=CH—C(=O)NH₂ | H | (E) |
| 254 | —CH=CH—C(=O)NH₂ | H | (E) HCl |

*(MH⁺) defines the mass of the protonated compound; it was determined with a MicroMass spectrometer equipped with an electrospray probe with a quadripolar analyser.

TABLE 2

[Structure: 2,6-dimethyl-R3-phenoxy-pyrimidine-NR1-phenyl-CN]

| Comp No. | R³ | R¹ | Physical data mp. °C./(MH+)* |
|---|---|---|---|
| 25 | —CH=CH—CN | H | mp. 256° C. |
| 99 | —CH₂—CN | H | mp. 184° C. |
| 100 | —CH₂—N(CH₂—CH₃)₂ | H | mp. 172° C. |
| 102 | —CH₂—CH₂—CN | H | mp. 224° C. |
| 101 | —CH₂—N(CH₃)—CH₂—CH₂—CN | H | mp. 196° C. |
| 26 | —CH=CH—CN | CH₃ | mp. 195° C. |
| 169 | —C(=O)—N(CH₂—CH₃)₂ | H | mp. 172° C. |
| 170 | —CH₂—N(CH₃)—CH₂—CN | H | |
| 171 | [pyrrolyl-CH₂-] | H | (398) |
| 172 | [thien-3-yl] | H | mp. 158° C. |
| 173 | —CH₂—N(CH₃)—CH₂—CH₂—N(CH₃)₂ | H | mp. 196° C. |
| 174 | —CH₂—N(CH₃)—CH=N—CN | H | mp. 254° C. |
| 175 | 2-furanyl | CH₃ | mp. 178° C. |

TABLE 2-continued

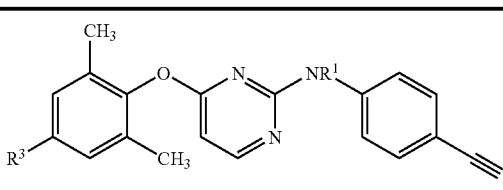

| Comp No. | R³ | R¹ | Physical data mp. °C./(MH+)* |
|---|---|---|---|
| 118 | 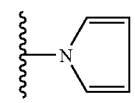 | H | 164° C. |
| 176 | 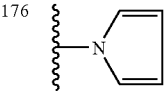 | CH₃ | mp. 188° C. |
| 177 | —CH=CH—Br | H | (Z), mp. 169° C. |
| 110 | —CH=C(F)—CN | H | (E), mp. 254° C. |
| 178 | —CH=C(CH₃)—CN | H | (Z) |
| 179 | —CH=C(CH₃)—CN | H | (E) |
| 180 | 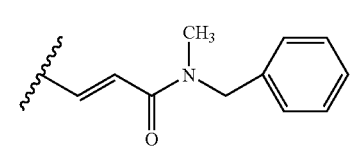 [SMILES: */C=C/C(=O)N(C)Cc1ccccc1] | H | (E) |
| 181 | —CH=CH—C(=O)—NH-cyclopropyl | H | (E) (426) |
| 182 | —CH=CH—C(=O)—NH—CH₂—CH₂—N(CH₃)₂ | H | (E) (427) |
| 183 | —CH=CH—C(=O)—NH—CH₂—CH₂—CH₂—O—CH₃ | H | (E)(458) |
| 184 | —CH=CH—C(=O)—NH—CH₂—CH(CH₃)₂ | H | (E)(442) |
| 185 | —CH=CH—C(=O)—NH—CH₂—CH₂—CN | H | (E)439 |
| 186 | 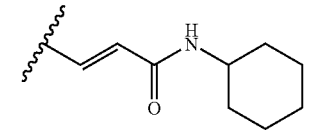 [SMILES: */C=C/C(=O)NC1CCCCC1] | H | (E)(468) |
| 187 | —CH=CH—C(=O)—NH—CH₂—CH₂—CH₂—N(CH₃)₂ | H | (E)(471) |
| 188 | —CH=CH—C(=O)—NH—(CH₂)₃—O—CH₂—CH₃ | H | (E)(472) |
| 189 | —CH=CH—C(=O)—NH—CH₂—CH₃ | H | (E)(414) |
| 190 | —CH=CH—C(=O)—NH—CH₂—CH₂—O—CH₃ | H | (E)(444) |
| 191 | —CH=CH—C(=O)—NH—CH(CH₃)₂ | H | (E)(428) |
| 192 | 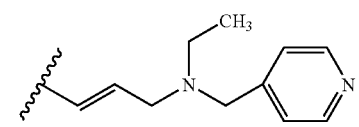 [SMILES: */C=C/CN(CC)Cc1ccncc1] | H | (E)(491) |
| 193 | 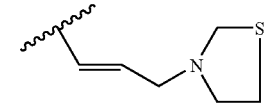 [SMILES: */C=C/CN1CCSC1] | H | (E)(444) |
| 194 | —CH=CH—CH₂—N(CH₃)—CH₂—CH₂—CN | H | (E)(439) |
| 195 | 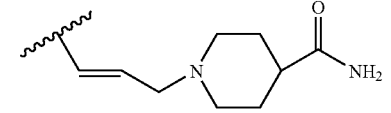 | H | (E)(483) |
| 196 | —CH=CH—CH₂—N(CH₂—CH₂—O—CH₃)₂ | H | (E)(488) |

TABLE 2-continued

[Structure: 2,6-dimethyl-4-R³-phenoxy group attached to pyrimidine at position 4; pyrimidine position 2 has NR¹ linked to 4-cyanophenyl]

| Comp No. | R³ | R¹ | Physical data mp. ° C./(MH+)* |
|---|---|---|---|
| 197 | [structure: —CH=CH—CH₂—N(CH₃)—CH₂—phenyl] | H | (E)(476) |
| 198 | —CH=CH—CH₂—N(CH₃)—CH₂—CH₂—CH₃ | H | (E)(428) |
| 199 | —CH=CH—CH₂—N(CH₃)—CH₂—CH₂—N(CH₂—CH₃)₂ | H | (E)(485) |
| 200 | —CH=CH—CH₂—N(CH₂—CH₃)—CH₃ | H | (E)(414) |
| 201 | —CH=CH—CH₂—N(CH₂—CH₂—CH₃)₂ | H | (E)(456) |
| 202 | —CH=CH—CH₂—N(CH₃)—CH₂—CH₂—CH₂—CH₃ | H | (E)(442) |
| 203 | [structure: —CH=CH—CH₂—N(tetrahydropyridine)] | H | (E)(438) |
| 204 | [structure: —CH=CH—CH₂—N(morpholine)] | H | (E)(442) |
| 205 | [structure: —CH=CH—CH₂—N(4-methylpiperazine)] | H | (E)(455) |
| 206 | —CH=CH—CH₂—N(benzyl)-CH₂—CH₂—N(CH₃)₂ | H | (E)(533) |
| 207 | —CH=CH—CH₂—N(CH₃)₂ | H | (E)(457) |
| 208 | —CH=CH—CH₂—N(isopropyl)₂ | H | (E)(456) |
| 121 | —CH=CH—C(=O)—NH₂ | H | (E) |
| 209 | [structure: —CH=CH—C(=O)—N(2,5-dihydropyrrole)] | H | (E), mp. 116° C. |
| 210 | [structure: —CH=CH—C(=O)—N(CH₃)—(1-methylpiperidin-4-yl)] | H | (E), mp. 254° C. |
| 211 | —CH=CH—C(=O)—N(CH₃)—CH₂—CH₂—OH | H | (E), mp. 222° C. |
| 212 | —CH=CH—C(=O)—N(CH₃)—CH₂—CN | H | (E), mp. 198° C. |
| 213 | —C(CH₃)=CH—CN | H | (E) |
| 214 | —CH=CH—C(=O)—N(CH₃)—CH₂—CH₂—CN | H | (E), mp. 204° C. |
| 215 | —CH=CH—C(=O)—N(CH₃)—CH₂—CH₃ | H | (E), mp. 211° C. |
| 216 | [structure: —CH=CH—C(=O)—N(morpholine)] | H | (E), mp. 246° C. |
| 217 | —CH=CH—C(=O)—N(CH₂CH₃)₂ | H | (E), mp. 226° C. |

TABLE 2-continued

[Structure: 2,6-dimethylphenyl with R³ at para position, connected via O to pyrimidine, which connects via NR¹ to 4-cyanophenyl]

| Comp No. | R³ | R¹ | Physical data mp. °C./(MH+)* |
|---|---|---|---|
| 218 | [structure: -CH=CH-C(=O)-N-piperidine] | H | (E), mp. 196° C. |
| 219 | —CH=CH—C(=O)—N(CH₃)₂ | H | (E), mp. 225° C. |
| 220 | —CH=C(CN)—CH₂—CN | H | (Z), mp. 195° C. |
| 109 | —CH=CH—Cl | H | (E), mp. 200° C. |
| 108 | —CH=CH—Cl | H | (Z), mp. 165° C. |
| 221 | —CH=CH—C(=O)—NH—CH₃ | H | (E), mp. 260° C. |
| 222 | —CH=CH—C(=O)—N(CH₂—CH₂—O—CH₃)₂ | H | (E), mp. 158° C. |
| 223 | [structure: -CH=CH-C(=O)-N-thiomorpholine] | H | (E), mp. 208° C. |
| 224 | [structure: -CH=CH-C(=O)-N(CH₃)-CH₂-CH₂-phenyl] | H | (E), mp. 208° C. |
| 113 | —CH=CH—C(=O)—N(CH₃)—CH₂—CH₂—CH₂—CH₃ | H | (E), mp. 212° C. |
| 225 | —CH₂—N(CH₂—CH₂—CN)₂ | H | mp. 154° C. |
| 226 | 2-furanyl | H | mp. 162° C. |
| 255 | —CH=CH—CN | H | (E) |

*(MH⁺) defines the mass of the protonated compound; it was determined with a MicroMass spectrometer equipped with an electrospray probe with a quadripolar analyser.

TABLE 3

[Structure: trisubstituted phenyl (R³, R⁴ᵃ, R⁴ᵇ) connected via X¹ to pyrimidine, which connects via NH to 4-cyanophenyl]

| Comp No. | R³ | R⁴ᵃ | R⁴ᵇ | X¹ | Physical data mp. °C. |
|---|---|---|---|---|---|
| 227 | —CH₂—CH₂—CN | CH₃ | H | —NH | mp. 186° C. |
| 228 | —CH₂—N(CH₃)—CH₂—CN | CH₃ | H | —NH | mp. 138° C. |
| 229 | —CH=C(CH₃)—CN | CH₃ | H | —NH | mp. 190° C. |
| 230 | —CH=CH—CN | CH₃ | H | —O— | (E), mp. 254° C. |
| 231 | —CH=C(CH₃)—CN | CH₃ | H | —O— | mp. 150° C. |
| 232 | —C(CH₃)=CH—CN | CH₃ | H | —O— | (E), mp. 234° C. |
| 105 | —CH₂—O—CH₂—CH₃ | CH₃ | H | —O— | mp. 140° C. |
| 233 | —CH=C(CH₃)—CN | CH₃ | Cl | —NH | mp. 214° C. |
| 234 | —CH₂—CH₂—CN | CH₃ | H | —O— | mp. 199° C. |
| 235 | —CH(CH₃)—CH₂—CN | CH₃ | H | —O— | mp. 195° C. |
| 236 | —CH₂—CH(CH₃)—CN | CH₃ | H | —O— | mp. 161° C. |
| 237 | —CH=CH—CN | CH₃ | H | —NH | (E), mp. > 264° C. |
| 238 | —CH₂—CN | CH₃ | Cl | —NH | mp. 184° C. |
| 239 | —CH=CH—CN | CH₃ | 2-furanyl | —NH | (E) mp. 175° C. |
| 119 | —CH=C(CN)—CH₂—CN | CH₃ | 2-furanyl | —NH | |

TABLE 3-continued

[Structure: pyrimidine core with R4a, R4b, R3 substituents on left phenyl connected via X1, and 4-cyanophenyl-NH on the right]

| Comp No. | R³ | R⁴ᵃ | R⁴ᵇ | X¹ | Physical data mp. °C. |
|---|---|---|---|---|---|
| 240 | [CH=CH-pyridinyl group] | CH₃ | Cl | —NH | mp. 248° C. Z/E = 50/50 |
| 241 | —CH₂—N(CH₃)—CH₂—CH₂—CN | CH₃ | Br | —NH | mp. 148° C. |
| 242 | —CH=CH—N | H | isopropyl | —NH | (E) 30%-(Z) 70% |
| 243 | —CH₂—N(CH₃)—CH₂—CH₂—CN | CH₃ | Cl | —NH | mp. 85° C. |
| 244 | —CH=CH—CN | H | Br | —NH | (E), mp. 270° C. |
| 245 | —CH=CH—CN | H | —OCH₃ | —NH | (E), mp. 258° C. |
| 246 | —C(CH₃)=C(CH₃)—CN | CH₃ | H | —O— | (E), mp. 214° C. |
| 247 | —CH=C(CH₃)—CN | CH₃ | Br | —NH | mp. 212° C. |
| 248 | —CH=CH—CN | CH₃ | Br | —NH | (E), mp. 250° C. |
| 249 | —CH=C(CH₃)—CN | H | —OCH₃ | —NH | mp. 166° C. |
| 250 | —CH=C(CH₃)—CN | H | Br | —NH | mp. 186° C. |
| 251 | —CH₂—CH₂—CN | H | —OCH₃ | —NH | mp. 228° C. |
| 252 | —CH₂—O—CH₂—CH₂—CN | H | Cl | —NH | mp. 168° C. |
| 133 | —CH=CH—CN | CH₃ | Cl | —NH | (E), mp, 258° C. |

PHARMACOLOGICAL EXAMPLE

A) In Vitro Models to Test the Ability of Compounds to Prevent HIV Infection Via Sexual Intercourse or Related Intimate Contact Between Partners In order to demonstrate the ability of the present compounds to prevent HIV infection via sexual intercourse or related intimate contact between partners, the compounds of formula (I) are tested in the following test. Immature monocyte derived dendritic cells (immMO-DC) represent a good model for interstitial dendritic cells, which are early targets during sexual HIV transmission and important initiators of the immune response. These immMO-DC were used in "in vitro" models to test the prevention of HIV infection via sexual intercourse or related intimate contact between partners.

In Vitro Model a)

The monotropic HIV strain Ba-L is pre-incubated with the compound of formula (I) (test compound). To the mixture of virus and test compound, immMO-DC are added and incubated for 2 hours at 37° C. After infection, cells are washed 6 times and cultured with autologous CD4(+) T cells (ratio immMO-DC/CD4(+) T: 1/10). Test compound is re-added and remains present during 14 days of primary culture, after which cells are extensively washed and PHA/IL-2 stimulated blasts are added (secondary culture, no test compound present). Supernatants are analysed in ELISA during primary and secondary culture. To determine antiviral activity, the test compound concentration able to suppress 50% of the viral replication at the end of the primary cultures (EC50) is measured. Additionally, cells are harvested after 3 weeks of secondary culture and analysed for the presence of HIV proviral DNA (PCR), to check for sterilisation and exclude viral rescue.

In Vitro Model b) (24 Hour Infection Experiment)

Monocyte-derived dendritic cells (MO-DC) were co-cultured with autologous T4 cells and infected with HIV strain Ba-L at a multiplicity of infection (MOI) of $10^{-3}$. A serial dilution of test compound was added at the time of infection. After 24 hours, 96-well plates were washed 3 times (test compound and free virus washed away) and medium (without test compound) was added. Half of the medium was refreshed twice a week. Culture supernatants were harvested after 7 and 14 days of culture. After 14 days, cultures were washed 3 times and PHA/IL-2 stimulated PBMC were added for a secondary culture to check for viral rescue. During secondary culture, half of the medium was refreshed twice weekly (IL-2 medium, without test compound). Supernatants were harvested after 1 and 2 weeks of secondary culture. After 2 weeks of secondary culture, cells were also harvested for PCR analysis. Supernatants were analysed in ELISA for the presence of HIV proviral DNA during primary and secondary culture.

After 7 days of primary culture, none out of 6 cups tested positive in ELISA for compound 230 for concentrations ranging from 10,000 to 100 nM. After 7 days of primary culture, none out of 6 cups tested positive in ELISA for compound 255 for concentrations ranging from 10,000 to 10 nM.

In Vitro Model c) (Standard Infection Experiment)

Monocyte-derived dendritic cells (MO-DC) were infected for 2 hours with the monotropic HIV strain Ba-L at a multiplicity of infection (MOI) of $10^{-3}$. After infection, cells were washed 6 times and resuspended in 10% BCS at 400.000 cells/ml. Autologous CD4(+) T cells were purified out of the lymphocyte fraction of the same elutration as the MO-DC and used at a concentration of $2 \times 10^6$ cells/ml ((ratio MO-DC/CD4(+) T: 1/5).

A serial dilution of a compound of formula (I) (test compound) was added to the MO-DC/CD4(+) T cell co-cultures. Each experiment was done in 96-well plates, in which each cup contained 50 µl of MO-DC, 50 µl of CD4(+) T cells and 100 μl of test compound. Half of the culture medium, with test compound, was refreshed twice weekly, during 14 days. Supernatants were analysed by ELISA after 14 days of culture for the presence of HIV antigens. To determine antiviral activity, the test compound concentration able to suppress 50% of the viral replication at the end of the primary cultures (EC50) was measured.

B) Immune Suppressive Activity of the Present Compounds Tested in Mixed Leucocyte Culture (MLC)

The compounds of formula (I) were tested for their immune-suppressive activity (defined as $ISC_{50}$ value) in a classical MLC in which monocyte-derived dendritic cells (MO-DC) were used as stimulators and allogenic CD4(+) T cells as responders.

A dilution series of test compound was added to the MO-DC/CD4(+) T cell co-cultures. After 5 days of culture, 20 μl of [methyl-3H]-Thymidine was added to each well and cultures were harvested after 7 hours. Analysis was done on a Topcount scintillation counter. The immune suppressive concentration ($ISC_{50}$) is defined as the test compound concentration inhibiting 50% of normal immune proliferation (test compound concentration inhibiting 50% of [methyl-3H]-Thymidine incorporation). (standard MLC assay)

For the 24 hour assay, the test compound was only present during the first 24 hours of the 5-day culture period. After 24 hours, the cultures were washed (three times) and culture medium without compound was added. The experimental set-up was from then on similar to the standard MLC assay described above.

Tables 4 and 5 list the results obtained in the above-indicated tests. From these results it can be concluded that the tested compounds efficiently block HIV infection in MO-DC/CD4(+) T cell co-cultures. Immune suppression was only found at much higher concentrations. Therefore, the compounds of the present invention can be considered as novel microbicides.

TABLE 4

| Comp. No. | $EC_{50}$ (nM) (in vitro model c)) | $ISC_{50}$ (nM) (Test B, standard assay)) |
| --- | --- | --- |
| 248 | 0.55 | 1,5553 |
| 24 | 0.55 | 675 |
| 151 | 2 | 385 |
| 231 | 3 | 18,690 |
| 1 | 0.42 | 1,216 |
| 230 | 0.24 | 43,208 |
| 162 | 5.5 | 1,141 |
| 250 | 3 | 4,500 |
| 242 | 3 | |
| 255 | 0.05 | 20,240 |

TABLE 5

| Comp. No. | $EC_{50}$ (nM) (in vitro model b)) | $ISC_{50}$ (nM) (Test B, 24 hour assay)) |
| --- | --- | --- |
| 1 | 1 | 22,221 |
| 230 | 8 | >100,000 |
| 255 | 2 | 24,635 |

The invention claimed is:
1. A method for the efficient blocking of transmission of HIV infection via sexual intercourse or related intimate contact between partners, said method comprising application to a contact site an effective amount of a compound having the formula

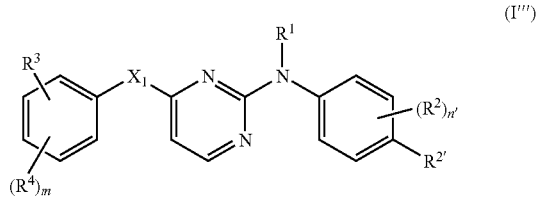

(I''')

an N-oxide, a pharmaceutically acceptable addition salt, a quaternary amine or a stereochemically isomeric form thereof;
wherein
n' is 0 or 1;
m is 1 or 2;
$R^4$ is independently $C_{1-6}$alkyl, nitro, amino, halo, or $C_{1-6}$alkyloxy;
$R^3$ is $C_{1-6}$alkyl substituted with cyano or $C_{2-6}$alkenyl substituted with cyano;
$X_1$ is —NH— or —O—;
$R^1$ is hydrogen;
$R^2$ is cyano; and
$R^{2'}$ is halo, $C_{1-6}$alkyl, trihalomethyl, trihalomethyloxy, cyano, aminocarbonyl, $C_{1-6}$alkyl substituted with cyano or aminocarbonyl.

2. The method of claim 1 wherein $R^{2'}$ is cyano, aminocarbonyl or $C_{1-6}$alkyl substituted with cyano or aminocarbonyl.

3. The method of claim 1 wherein $R^3$ is $C_{2-6}$alkenyl substituted with cyano.

4. The method of claim 1 wherein $R^3$ is ethenyl substituted with cyano.

5. The method of claim 1 wherein $R^3$ is ethyl substituted with cyano.

6. The method of claim 1 wherein the compound is selected from 4-[[4-[[4-(2-cyanoethenyl)-2,6-dimethylphenyl]amino]-2-pyrimidinyl]amino]-benzonitrile;

4-[[4-[4-(2-cyanoethenyl)-2,6-dimethylphenoxy]-2-pyrimidinyl]amino ]benzonitrile ; 4-[[4-[4-[2-cyanoethenyl]-2-methylphenoxy]-2-pyrimidinyl]amino]benzonitrile;

a N-oxide, a pharmaceutically acceptable addition salt, a quaternary amine or a stereochemically isomeric form thereof.

7. The method of claim 6, wherein the compound is

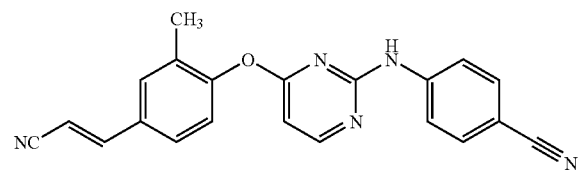

an N-oxide, a pharmaceutically acceptable addition salt, a quaternary amine or a stereochemically isomeric form thereof.

8. The method of claim 6, wherein the compound is

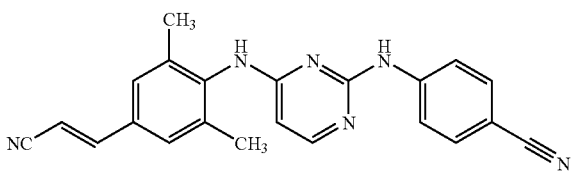

an N-oxide, a pharmaceutically acceptable addition salt, a quaternary amine or a stereochemically isomeric form thereof.

9. The method of claim 6, wherein the compound is

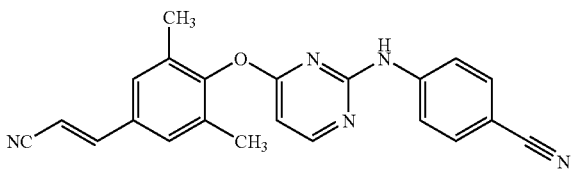

an N-oxide, a pharmaceutically acceptable addition salt, a quaternary amine or a stereochemically isomeric form thereof.

10. The method of claim 1 wherein the sexual intercourse is vaginal, anal or oral sex.

11. The method of claim 10 wherein the sexual intercourse is vaginal sex.

12. The method according to claim 1, wherein the contact site comprises a vagina, rectum, mouth or skin.

13. The method according to claim 1, wherein the compound comprises a composition in the form of a gel, jelly, cream, ointment, film, sponge, foam, intravaginal ring, cervical cap, suppository for rectal or vaginal application, vaginal or rectal or buccal tablet, or mouthwash.

14. The method according to claim 1, wherein the HIV infection is a multidrug resistant HIV infection.

15. A pharmaceutical composition comprising a pharmaceutically acceptable carrier and as active ingredient a therapeutically effective amount of a compound defined in claim 1, wherein the pharmaceutical composition comprises a gel comprising carbopol, hydroxypropyl cellulose, hydroxyethyl cellulose or pregelatinized starch.

16. A pharmaceutical composition according to claim 15, further comprising one or more additional antiretroviral compounds.

17. A pharmaceutical composition according to claim 15, further comprising one or more components selected from an antibody, a detergent or surfactant, a coating for the contact site of administration of the pharmaceutical composition, a peptide or a pH regulator.

18. A pharmaceutical composition according to claim 15, further comprising a spermicidal compound.

* * * * *